US005626557A

United States Patent [19]
Mann

[11] Patent Number: 5,626,557
[45] Date of Patent: *May 6, 1997

[54] KNEE BRACE HAVING AN INFLATABLE BLADDER AND EXTERIOR SUPPORT ELEMENT

[75] Inventor: Donaerl B. Mann, Ft. White, Fla.

[73] Assignee: D'Mannco, Inc, High Springs, Fla.

[*] Notice: The portion of the term of this patent subsequent to Aug. 22, 2014, has been disclaimed.

[21] Appl. No.: 583,849

[22] Filed: Jan. 11, 1996

[51] Int. Cl.⁶ .................................................. A61F 5/00
[52] U.S. Cl. ............................ 602/26; 602/16; 602/13
[58] Field of Search .............................. 602/5, 13, 16, 602/20, 23, 26, 60–63

[56] References Cited

U.S. PATENT DOCUMENTS

| | | | |
|---|---|---|---|
| 1,601,659 | 9/1926 | Van Harlingen | 602/62 |
| 3,804,084 | 4/1974 | Lehman | 602/62 X |
| 3,993,056 | 11/1976 | Rabischong et al. | . |
| 4,064,874 | 12/1977 | Valin | 602/26 |
| 4,340,042 | 7/1982 | Smith | . |
| 4,353,362 | 10/1982 | DeMarco | . |
| 4,366,813 | 1/1983 | Nelson | 602/26 |
| 4,379,463 | 4/1983 | Meier et al. | . |
| 4,872,448 | 10/1989 | Johnson, Jr. | . |
| 4,887,590 | 12/1989 | Logue et al. | 602/26 |
| 4,938,207 | 7/1990 | Vargo | 602/26 |
| 4,947,834 | 8/1990 | Kartheus et al. | . |
| 5,036,837 | 8/1991 | Mitchell et al. | 602/26 X |
| 5,261,871 | 11/1993 | Greenfield | 602/62 X |
| 5,334,135 | 8/1994 | Grim et al. | 602/62 X |
| 5,385,538 | 1/1995 | Mann | . |
| 5,399,153 | 3/1995 | Caprio, Jr. et al. | 602/63 X |
| 5,451,201 | 9/1995 | Prengler | 602/13 X |
| 5,462,517 | 10/1995 | Mann | . |

Primary Examiner—Linda C. Dvorak
Attorney, Agent, or Firm—Larson & Larson, P.A.; Herbert W. Larson

[57] ABSTRACT

A cloth body having a central knee hole wrapped around a patient's knee to treat knee flexion contractures. Hook and loop straps secure the cloth body to the patient's knee. Longitudinally extending pockets on opposite sides of the knee hole contain an air bladder. Inflation of the air bladder supports the patient's knee in a rigid position. End pockets integral with the cloth body and adjacent the longitudinally extending pockets enclose end portions of a support element.

20 Claims, 4 Drawing Sheets

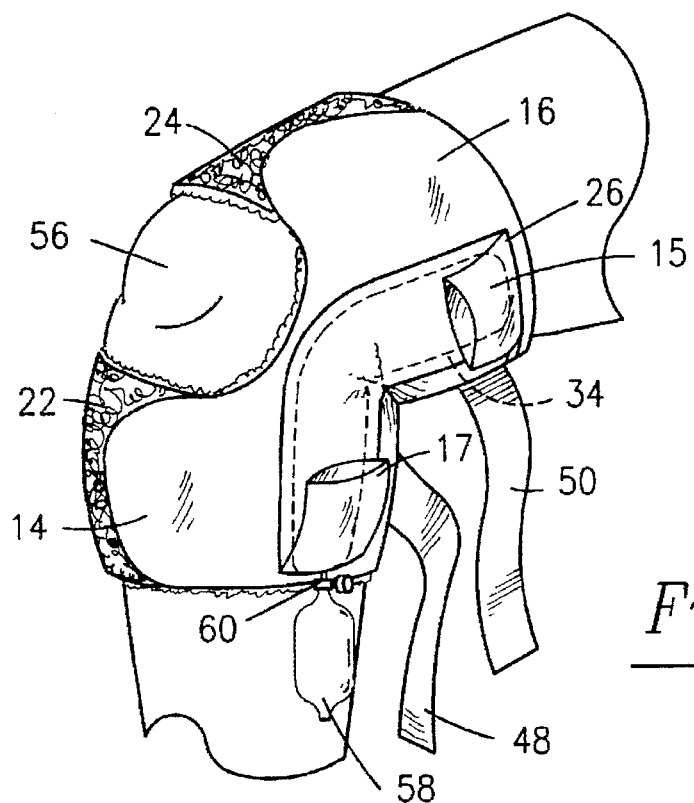
Fig. 3
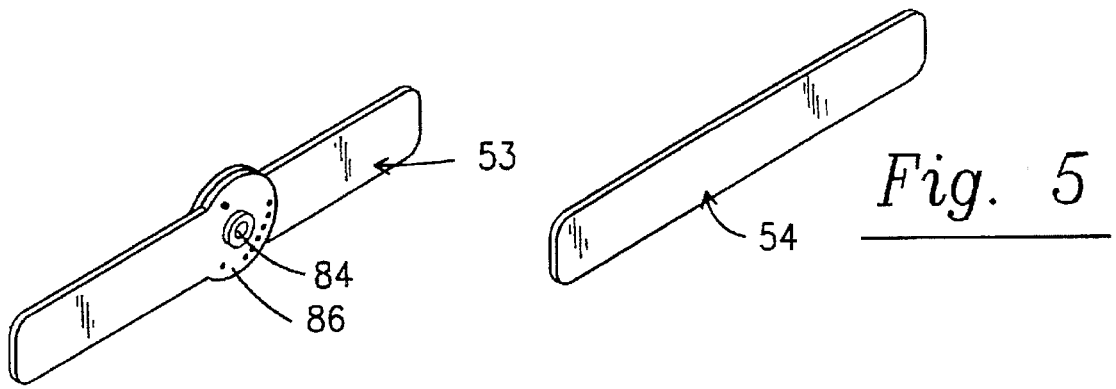
Fig. 5
Fig. 4
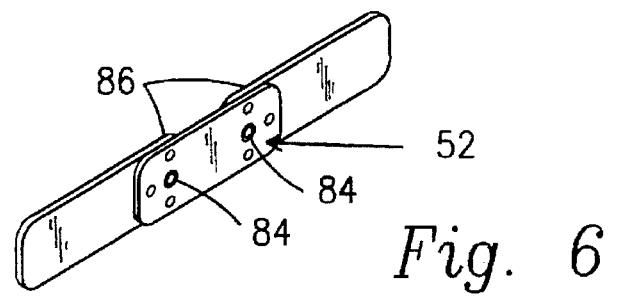
Fig. 6

5,626,557

KNEE BRACE HAVING AN INFLATABLE BLADDER AND EXTERIOR SUPPORT ELEMENT

PRIOR APPLICATIONS

This application is related to U.S. Pat. Nos. 5,385,538 and 5,462,517.

BACKGROUND OF THE INVENTION

1. Field of the Invention

This invention relates to orthopedic knee brace appliances. More particularly it refers to an orthopedic appliance applied to a patient's knee, the appliance containing an air bladder inflated to retain the knee in a rigid configuration.

2. Description of Prior Art

Many orthopedic appliances exist containing air bladders or fluid control chambers for intermittently supporting and releasing support on body parts. U.S. Pat. No. 3,993,056 describes such appliances having inflatable tubes stitched into a fabric extending vertically over a portion of the fabric. U.S. Pat. No. 4,430,042 describes a pillow type device strapped to a leg and then inflated. U.S. Pat. No. 4,872,448 describes a U-shaped inflatable air bladder over the patella. U.S. Pat. No. 4,938,207 describes a linear brace employing first and second fluid filled chambers. U.S. Pat. No. 4,947,834 describes a brace for compressing a patient's outer extremities, the brace having flexible chambers arranged one after another in a series and these are successively inflated. U.S. Pat. No. 4,960,115 describes a body support apparatus having at least two inflation chambers.

None of these appliances provides a means to alternately support a patient's knee in various positions and permit easy removal and reapplication of the splint for treating wounds under the brace. A need exists to have flexibility in a knee brace support appliance for treating knee flexion contractures and to obtain ease of removing and reapplying the brace.

SUMMARY OF THE INVENTION

I have invented a knee brace having an inflatable bladder support to treat knee flexion contractures. My knee brace has a cloth body having a soft bottom portion in contact with the patient's skin and a fabric top surface to which longitudinal pockets are attached, each longitudinal pocket containing a plastic air bladder. Mounted exterior and adjacent to the pocket is either a rigid support or a hinged support element. Hook and loop straps are attached to the top surface and an area from which a patella portion of the knee can protrude is provided. A hand pump is attached to the bladder to inflate or deflate the bladder as needed by the patient. The wrap around fastening of the cloth body allows for treatment of wounds and incisions by unfastening the hook and loop closures, treating the wound, and easily reapplying the brace. Straps having hook and loop material are attached to the top surface of the cloth body providing a means to secure the appliance around the knee of a patient.

BRIEF DESCRIPTION OF THE DRAWINGS

The invention may be best understood by those having ordinary skill in the art by reference to the following detailed description when considered in conjunction with the accompanying drawings in which:

FIG. 3 is a perspective view of the knee brace appliance positioned on a patient's knee with an air bladder shown in phantom and the empty end pockets for insertion of the support element.

FIG. 4 is a perspective view of a hinged support element.

FIG. 5 is a perspective view of a rigid support element.

FIG. 6 is a perspective view of a polycentric support element.

DETAILED DESCRIPTION OF THE INVENTION

Figure 1:
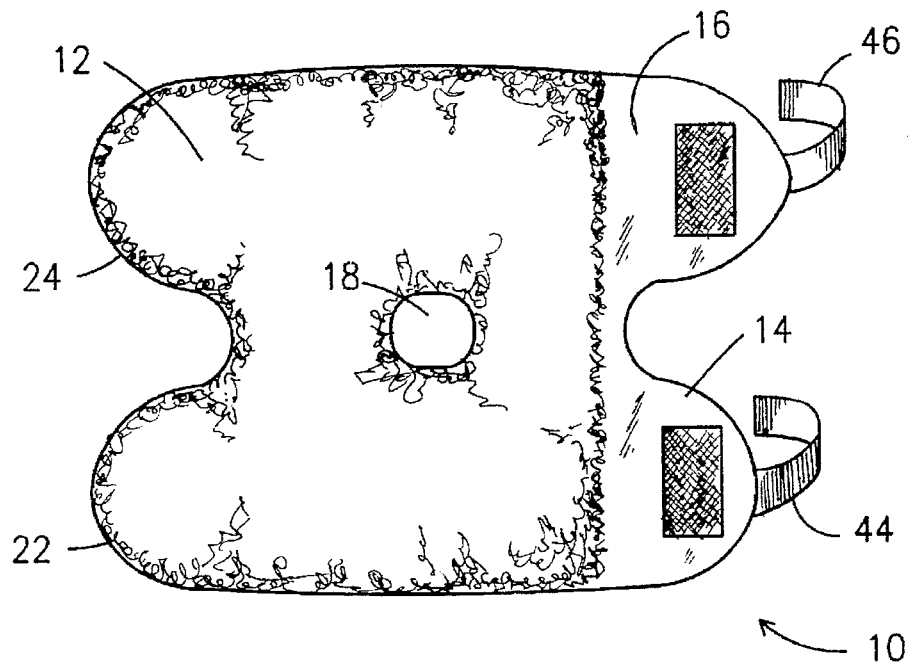
FIG. 1 is a bottom plan view of the knee brace appliance of my invention prior to applying the appliance to a patient.

Throughout the following detailed description, the same reference numerals refer to the same elements in all figures.

The knee brace 10 is shown in FIG. 1 presenting a bottom plan view thereof. The bottom portion is covered by a pile 12 such as KODEL, a registered trademark for a product sold by Eastman Kodak Company, or other soft wool or wool like material which will not be abrasive to a patient's skin surface. A short section 14 and a longer section 16 projecting from the pile 12 of hook and loop material are used in fastening the brace 10 to a patient's knee. A hole 18 approximately centrally located in the pile material 12 exposes a posterior portion of the knee.

Figure 2:
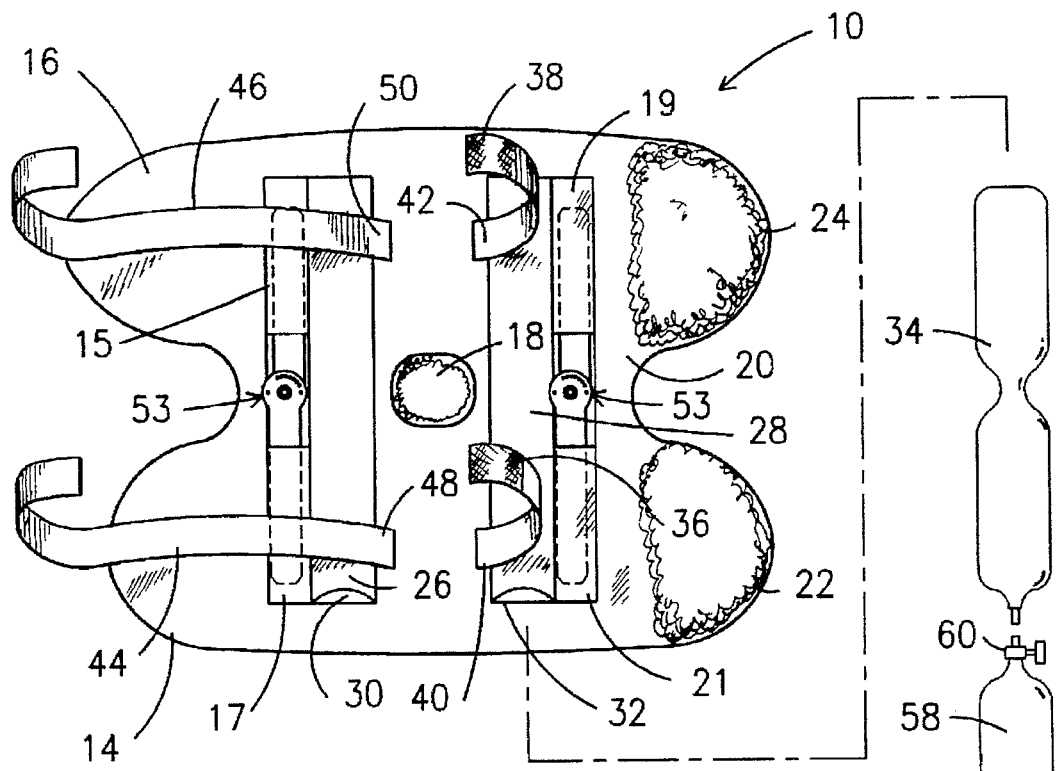
FIG. 2 is a top plan view of the knee brace appliance shown in FIG. 1.

FIG. 2 shows a top plan view of the knee brace 10. The top surface of the brace is covered by tightly woven fabric 20. A pair of projecting sections 22 and 24, oppositely positioned sections 14 and 16 respectively, have hook and loop material attached by sewing to the tightly woven fabric 20. As shown in FIG. 1, the bottom portions of sections 22 and 24 are covered by the pile 12. Also shown in FIG. 2 is a pair of pockets 26 and 28 respectively sewn to the top surface of the fabric 20. An opening 30 to pocket 26 and an opening 32 to pocket 28 provides a means for inserting an air bladder 34 into each pocket. Straps 40 and 42 are also sewn on to the fabric 20 with the bottom surface 36 and 38 respectively of straps 40 and 42 covered with hook and loop material. A top surface 44 and 46 respectively of straps 48 and 50 are covered by hook and loop material. The reverse side of each strap 48 and 50 has a cloth material. The top surface of projecting sections 14 and 16 are covered by fabric material. End pockets 15, 17, 19 and 21 are sewn onto surface fabric 20 adjacent pockets 26 and 28 for the purpose of retaining a hinged support element 53 adjacent a longitudinal pocket. In addition to hinged support element 53, either a polycentric support element 52 or a rigid support element 54, as shown respectively in FIGS. 6 and 5, are insertable into end pockets 15 and 17 and 19 and 21.

The preferred shape of the air bladder 34 is "hour-glass", although air bladders of other shapes could be employed with brace 10. This "hour-glass" shape is ideal to the configuration of brace 10 whereby an upper portion of the air bladder 34 lays against a lateral portion of the thigh above the knee and a lower portion of the air bladder 34 lays against a lateral portion of the calf below the knee.

FIG. 3 shows the brace 10 mounted over the knee 56 of a patient. Section 16 is folded over on to section 24 so that the hook and loop material on the bottom of section 16 engages the hook and loop material on the top of section 24. In like manner, the section 14 is passed over section 22 so that the hook and loop material on the bottom portion of section 14 engages the corresponding hook and loop material on the top portion of section 22. In the brace 10, shown in FIG. 3, a hinged 53 or a polycentric support element 52 would be inserted into end pockets 15 and 17 so that the patient can bend his or her leg. A bulb pump 58 is attached by its valve 60 to the corresponding valve opening in bladder 34 to enable the bladder to be expanded and rigidly support the patient's knee 56 in the designated position.

Figure 8:
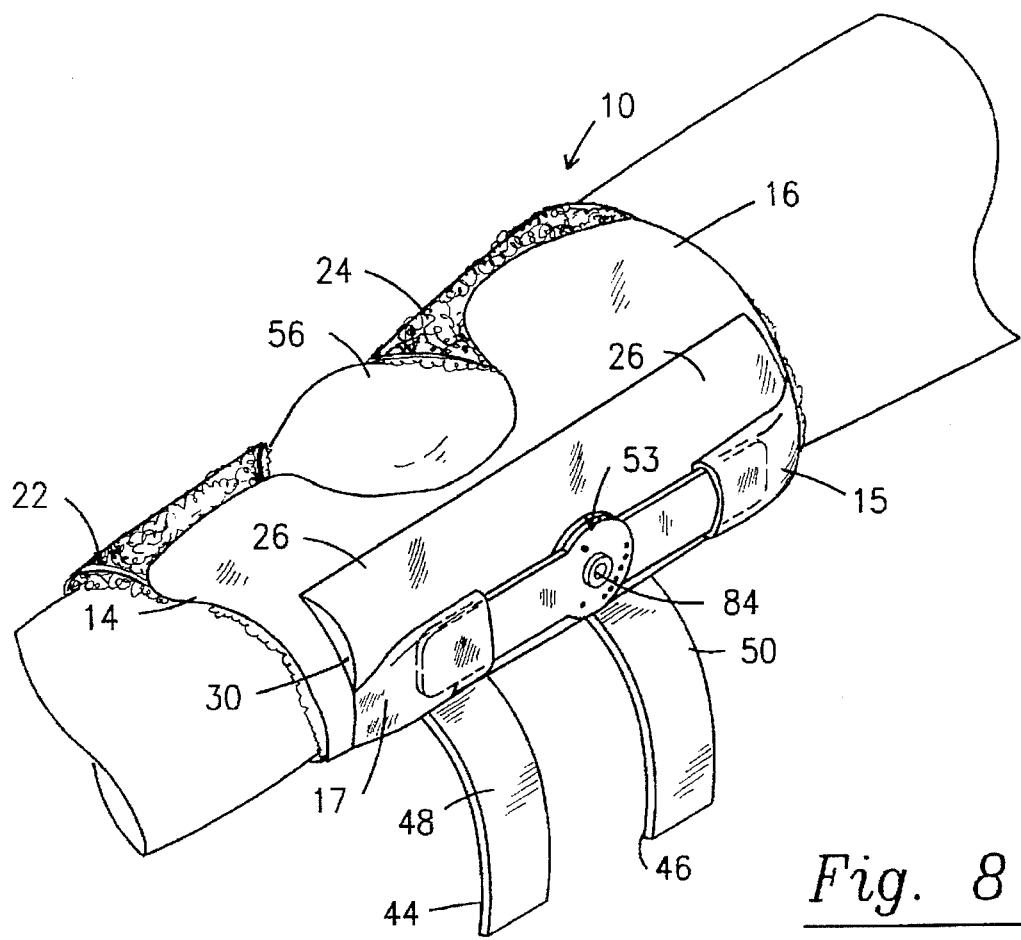
FIG. 8 is a perspective view of the knee brace shown in FIG. 1, and the hinged support element retaining a patient's knee in a fixed position.

As shown in FIG. 8, a hinged rigid support element 53 is employed in end pockets 15 and 17 which act together with a bladder 34 in pocket 26 inserted through hole 30 to maintain a completely rigid configuration for the patient's leg. Top surfaces 44 and 46 of straps 48 and 50 respectively are attached to corresponding hook and loop material 36 and 38 on straps 40 and 42 respectively by wrapping around the patient's leg. This produces a configuration where the patient's leg is extended in a fixed position with the bladder 34 filled to maintain the leg in the fixed position. The wrapping leaves an area for the patella of the patient's knee 56 to protrude. Other types of straps can be substituted for the hook and loop straps such as buckled straps and straps containing eyes with corresponding pegs to properly hold the knee brace in place.

Figure 9:
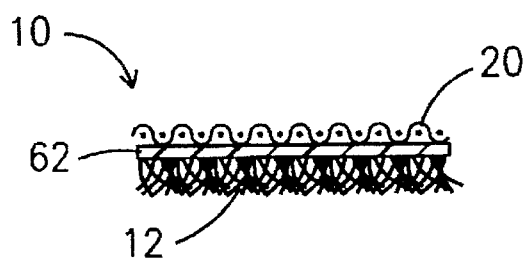
FIG. 9 is a cross sectional view through the cloth body of the knee brace appliance shown in FIG. 1.

As shown in FIG. 9, the top surface of tightly woven fabric 20 is separated from the bottom portion covered by a pile 12 by an intermediate foam layer 62 so that the brace 10 has a soft wool-like material 12 in contact with the skin and a durable fabric 20 on the outside protecting the brace from environmental effects, but with a foam intermediate material to maintain the body structure of the splint while at the same time providing a soft medium to prevent pressure against the soft tissue of the leg.

The knee brace 10 of this invention is designed primarily to treat pre-fixed contracture of the knee. Such pre-fixed contracture is any contracted joint that can be flexed or extended and where splinting is indicated for treatment. The brace 10 will stabilize the extension of the knee and is useful for immobilization of the knee during post-trauma or post-surgery. In addition, the brace 10 will support post-trauma or surgery patients while undergoing rehabilitation.

Figure 10:
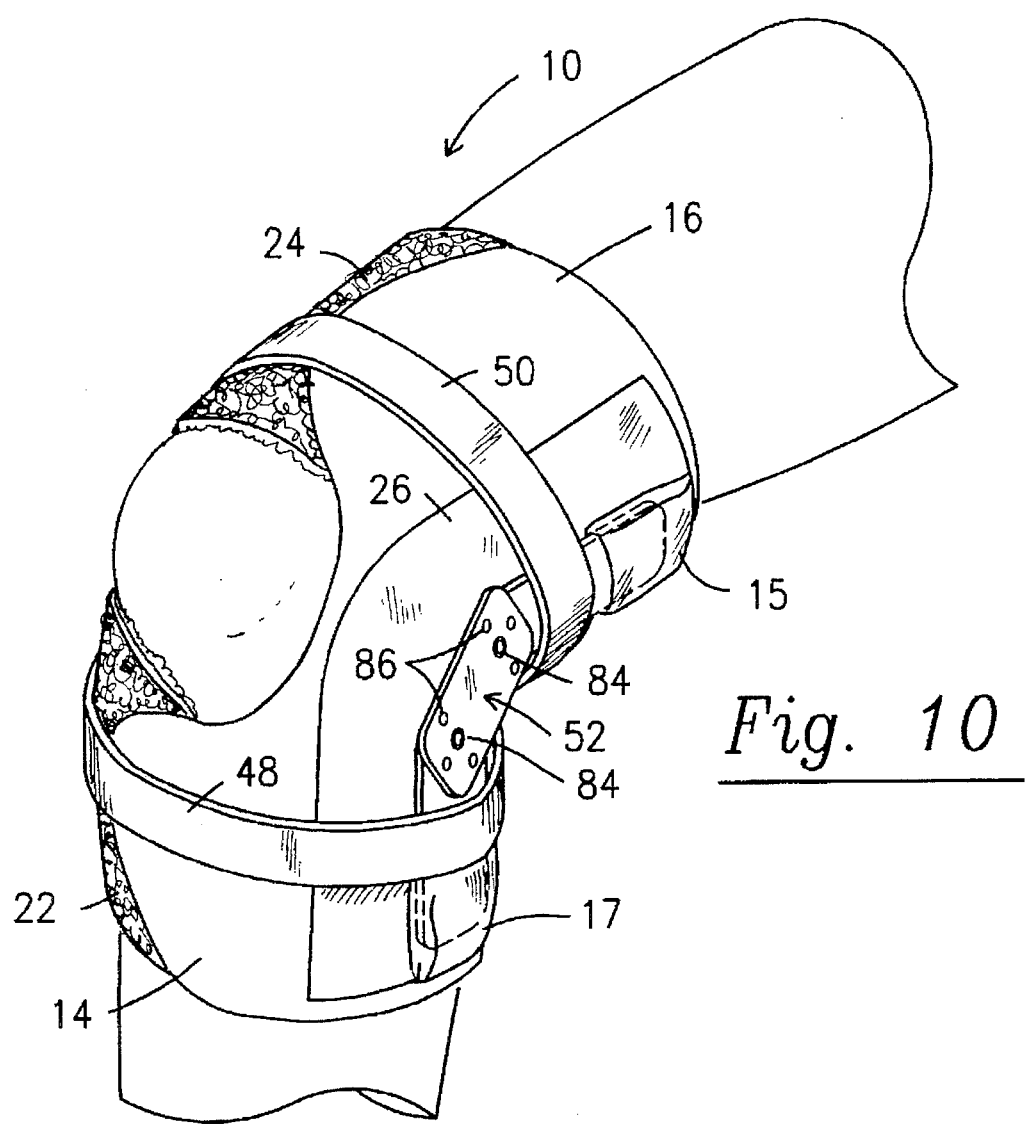
FIG. 10 is a perspective view of the knee brace appliance positioned on a patient's bent knee wrapped with hook and loop straps and with an air bladder in the pocket and polycentric support element exterior to the air bladder pocket.

In placing the brace 10 on a patient, the leg is extended as far as comfort will allow and the open brace 10 is place on the patient's knee with the section 16 placed around the thigh to contact the section 24 on the fabric, and the section 14 placed around the calf to contact the section 22 on the fabric as shown in FIG. 8. The pile surface 12 is placed down over the patient's skin. The air bladder is inflated to hold the leg in the degree of extension desired. The greater the degree of extension, the more inflation in the air bladder 34. If the patient is ambulating, the polycentric support element 52 is used in the end pockets 15 and 17 and 19 and 21, as shown in FIG. 10, whereas if the knee should be completely immobilized, the rigid support elements 54 are inserted in end pockets 15 and 17 and 19 and 21. After the correct air pressure is reached, the pile straps 48 and 50 are connected to straps 40 and 42 respectively. Once the amount of air pressure necessary for either stabilization or immobilization has been determined, the splint can be removed and put back on without changing the air pressure in the air bladder 34. To remove the brace 10 the straps are all unfastened. To replace the brace 10, extend the leg and place the brace 10 pile side 12 toward and under the leg and fasten the wide straps over and under the knee. One finger should be inserted under all edges for correct clearance. The brace 10 can be easily removed and replaced in order to treat wounds under the splinted area.

FIG. 10 shows the knee flexed employing an exterior polycentric support element 52 with straps 48 and 50 wrapped over the top of the support elements 52.

The support elements 52 and 53 are generally made from stainless steel whereas support element 54 can be stainless steel or a stiff plastic.

Figure 7:
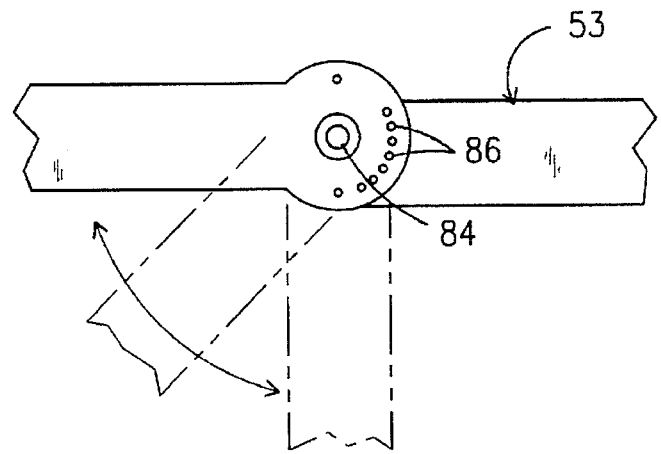
FIG. 7 is a view of a hinged support element showing different positions in phantom.

FIG. 7 illustrates the variety of fixed positions in which hinged support element 53 can be set. Polycentric support element 52 also allows the orthosis sis appliance 10 to be locked in a variety of fixed positions. Hinged support element 53 or polycentric support element 52 are locked in their respective fixed position by a preferred push button mechanism 84, although removable screws (not shown) could be employed to achieve the same result. The push button mechanism 84 is engagable from an inner surface along hinged support element 53 and polycentric support element 52. A plurality of Chicago screws 86 permit rotation of hinged support element 53 and polycentric support element 52.

The support elements 52 and 53 are generally made from stainless steel whereas support element 54 can be stainless steel or a stiff plastic.

Equivalent materials can be substituted for the materials employed in this invention to obtain substantially the same result in the same way.

Having thus described the invention what is claimed and desired to be secured by Letters Pat. No. is:

1. An orthopedic appliance for surrounding a knee of a patient to treat knee flexion contractures, the appliance comprising, a cloth body having a top and bottom layer, a foam layer located intermediate the top and bottom layers, and a generally centrally located hole, the top layer covered by a tightly woven fabric, the bottom layer covered by a soft non-abrasive material for contact with the skin of the patient, the cloth body wrapped around the knee of the patient such that an area is provided from which a patella portion of the knee can protrude and the centrally located hole exposes a posterior portion of the knee, means attached to the top layer of the cloth body for securing the cloth body in a wrapped position, at least two longitudinal pockets integrally attached to the top layer of the cloth body, each longitudinal pocket having an opening formed therein, an air bladder mounted within each longitudinal pocket, the air bladders permitting inflation to rigidly set the knee in a desired position and deflation so that the patient can flex the knee, the air bladders having been inserted through the openings in the longitudinal pockets, a support element adjacent at least one of the longitudinal pockets containing the air bladder and means for mounting the support element to the top layer of the cloth body adjacent the air bladder, the support element providing lateral and medial support to the knee of the patient.

2. The orthopedic appliance for surrounding a knee of a patient to treat knee flexion contractures according to claim 1, the appliance having two support elements, one support element mounted adjacent each longitudinal pocket on an exterior surface of the top layer of the cloth body.

3. The orthopedic appliance for surrounding a knee of a patient to treat knee flexion contractures according to claim 1, wherein the at least two longitudinal pockets are located on opposite sides of the generally centrally located hole.

4. The orthopedic appliance according to claim 3 wherein the means for mounting at least one support element is a pair of oppositely positioned end pockets attached to the top layer of the cloth body adjacent each longitudinal pocket containing an air bladder.

5. The orthopedic appliance for surrounding a knee of a patient to treat knee flexion contractures according to claim 1, wherein the means for mounting at least one support element is a pair of oppositely positioned end pockets attached to the top layer of the cloth body adjacent the longitudinal pocket containing an air bladder.

6. The orthopedic appliance for surrounding a knee of a patient to treat knee flexion contractures according to claim 1, wherein the at least one support element is polycentric to permit the patient's knee to be set in a variety of fixed positions.

7. The orthopedic appliance for surrounding a knee of a patient to treat knee flexion contractures according to claim 1, wherein the at least one support element is rigid to restrict movement of the knee, the longitudinal support element setting the knee in a straight and fixed position.

8. The orthopedic appliance for surrounding a knee of a patient to treat knee flexion contractures according to claim 1 wherein the means attached to the top layer of the cloth body for securing the cloth body in a wrapped position is hook and loop straps.

9. An orthopedic appliance for surrounding a knee of a patient to treat knee flexion contractures, the appliance comprising, a cloth body having a top and bottom layer, a foam layer located intermediate the top and bottom layers, and a generally centrally located hole, the top layer covered by a tightly woven fabric, the bottom layer covered by a soft non-abrasive material for contact with the skin of the patient, the cloth body wrapped around the knee of the patient such that an area is provided from which a patella portion of the knee can protrude and the centrally located hole exposes a posterior portion of the knee, means attached to the top layer of the cloth body for securing the cloth body in a wrapped position, two longitudinal pockets integrally attached to the top layer of the cloth body, each longitudinal pocket having an opening formed therein, an air bladder mounted within each longitudinal pocket, the air bladders permitting inflation to rigidly set the knee in a desired position and deflation so that the patient can flex the knee, the air bladders having been inserted through the openings in the longitudinal pockets, a support element adjacent each longitudinal pocket, and a pair of oppositely positioned end pockets integrally attached to the top layer of the cloth body adjacent to each longitudinal pocket for receiving end portions of the support element.

10. The orthopedic appliance for surrounding a knee of a patient to treat knee flexion contractures according to claim 9, wherein the support element received in each pair of end pockets is hinged to permit the patient's knee to be set in a variety of fixed positions.

11. The orthopedic appliance for surrounding a knee of a patient to treat knee flexion contractures according to claim 9, wherein the support element received in each pair of end pockets is rigid to restrict movement of the knee, the support elements setting the knee in a straight and fixed position.

12. The orthopedic appliance for surrounding a knee of a patient to treat knee flexion contractures according to claim 9, wherein the support element received in each pair of end pockets is polycentric to permit movement of the knee and to allow the knee to be set in a variety of fixed positions.

13. The orthopedic appliance for surrounding a knee of a patient to treat knee flexion contractures according to claim 9 wherein the means attached to the top layer of the cloth body for securing the cloth body in a wrapped position is hook and loop straps.

14. An orthopedic appliance for surrounding a knee of a patient to treat knee flexion contractures, the appliance comprising, a cloth body having a top and bottom layer, a foam layer located intermediate the top and bottom layers, and a generally centrally located hole, the top layer covered by a tightly woven fabric, the bottom layer covered by a soft non-abrasive material for contact with the skin of the patient, the cloth body wrapped around the knee of the patient such that an area is provided from which a patella portion of the knee can protrude and the centrally located hole exposes a posterior portion of the knee, hook and loop straps attached to the top layer of the cloth body for securing the cloth body in a wrapped position, two longitudinal pockets integrally attached to the top layer of the cloth body on opposed sides of the generally centrally located hole, each longitudinal pocket having an opening formed in an end portion, an air bladder mounted within each of the two longitudinal pockets, the air bladders permitting inflation to rigidly set the knee in a desired position and deflation so that the patient can flex the knee, the air bladders having been inserted through the openings in the longitudinal pockets, a longitudinal support element mounted adjacent each of the two longitudinal pockets for providing lateral support to the patient's knee, the longitudinal support elements being held in place by the hook and loop straps.

15. The orthopedic appliance for surrounding a knee of a patient to treat knee flexion contractures according to claim 14, wherein the longitudinal support elements are polycentric to permit the patient's knee to be set in a variety of fixed positions.

16. The orthopedic appliance for surrounding a knee of a patient to treat knee flexion contractures according to claim 14, wherein the longitudinal support elements are rigid to restrict movement of the knee, the longitudinal support elements setting the knee in a straight and fixed position.

17. The orthopedic appliance for surrounding a knee of a patient to treat knee flexion contractures according to claim 14, wherein the air bladders are hour-glass shaped.

18. The orthopedic appliance for surrounding a knee of a patient to treat knee flexion contractures according to claim 14, wherein the soft non-abrasive material on the bottom layer of the cloth body is a synthetic wool pile.

19. The orthopedic appliance for surrounding a knee of a patient to treat knee flexion contractures according to claim 14, wherein the air bladder contains a valve to permit ingress and egress of air.

20. The orthopedic appliance for surrounding a knee of a patient to treat knee flexion contractures according to claim 14 wherein each longitudinal support element is made of stainless steel.

* * * * *